United States Patent
Joo et al.

(10) Patent No.: US 9,594,026 B2
(45) Date of Patent: Mar. 14, 2017

(54) APPARATUS AND METHOD FOR MEASURING CONCENTRATION OF HEMOGLOBIN USING PHOTOTHERMAL EFFECT

(71) Applicant: INDUSTRY-ACADEMIC COOPERATION FOUNDATION YONSEI UNIVERSITY, Seoul (KR)

(72) Inventors: Chulmin Joo, Goyang-si (KR); Jinyeong Yim, Seoul (KR); Hun Kim, Incheon (KR); Su Ho Ryu, Seoul (KR)

(73) Assignee: INDUSTRY-ACADEMIC COOPERATION FOUNDATION YONSEI UNIVERSITY, Seoul (KR)

( * ) Notice: Subject to any disclaimer, the term of this patent is extended or adjusted under 35 U.S.C. 154(b) by 0 days.

(21) Appl. No.: 14/604,691

(22) Filed: Jan. 24, 2015

(65) Prior Publication Data
US 2015/0260645 A1   Sep. 17, 2015

(30) Foreign Application Priority Data
Mar. 13, 2014  (KR) .................... 10-2014-0029549

(51) Int. Cl.
*G01N 21/85* (2006.01)
*G01N 21/17* (2006.01)

(52) U.S. Cl.
CPC .......... *G01N 21/85* (2013.01); *G01N 21/171* (2013.01)

(58) Field of Classification Search
CPC .................................................. G01N 21/85
See application file for complete search history.

(56) References Cited

U.S. PATENT DOCUMENTS 7,005,982 B1 * 2/2006 Frank .............. G01N 21/35
340/539.17
2004/0239938 A1 * 12/2004 Izatt .............. G01B 9/02004
356/479

(Continued)

FOREIGN PATENT DOCUMENTS

EP          0049918 A1    4/1982
JP       2010-243311 A   10/2010

(Continued)

OTHER PUBLICATIONS

KIPO Office Action for Korean Patent Application No. 10-2014-0029549 which corresponds to the above-identified U.S. application.

(Continued)

*Primary Examiner* — Tarifur Chowdhury
*Assistant Examiner* — Omar Nixon
(74) *Attorney, Agent, or Firm* — LRK Patent Law Firm (57) ABSTRACT

The present invention relates to an apparatus for measuring concentration of hemoglobin in blood using a photothermal effect, the apparatus including: a reference light source unit for radiating a reference beam; a photothermal light source unit for radiating a photothermal beam from which the photothermal effect is generated; a cuvette unit for accommodating a collected blood sample thereinto and having first and second reflection layers; and a concentration operation unit for calculating the concentration of hemoglobin by using the phase changes of interference signals generated from the incidence of the reference beam radiated from the reference light source unit onto the first and second reflection layers of the cuvette unit as the photothermal beam radiated from the photothermal light source unit is incident onto the cuvette unit and absorbed by hemoglobin to generate the photothermal effect through the emission of heat.

14 Claims, 7 Drawing Sheets

(56) References Cited

U.S. PATENT DOCUMENTS

| | | | |
|---|---|---|---|
| 2006/0181708 A1* | 8/2006 | Takahashi | G01N 21/171 356/432 |
| 2008/0123099 A1* | 5/2008 | Takahashi | G01N 21/171 356/450 |
| 2009/0027654 A1* | 1/2009 | Takahashi | G01N 21/00 356/36 |
| 2009/0093807 A1* | 4/2009 | Hyde | A61B 5/0071 606/34 |
| 2011/0007317 A1* | 1/2011 | Ikebukuro | B01L 3/5027 356/432 |
| 2012/0010557 A1* | 1/2012 | Heger | A61K 9/1271 604/20 |
| 2012/0078160 A1 | 3/2012 | McMillan | |
| 2013/0006116 A1* | 1/2013 | Kim | A61B 5/0059 600/476 |
| 2014/0243805 A1* | 8/2014 | Dick | A61F 9/00823 606/11 |
| 2014/0268163 A1* | 9/2014 | Milner | A61B 3/102 356/451 |

FOREIGN PATENT DOCUMENTS

| | | |
|---|---|---|
| KR | 10-2002-0035101 A | 5/2002 |
| KR | 10-2002-0081763 A | 10/2002 |
| KR | 10-2011-0057341 A | 6/2011 |
| WO | 2012/075126 A2 | 6/2012 |

OTHER PUBLICATIONS

Jinyeong Yim et al., "Photothermal spectral-domain optical coherence reflectometry for direct measurement of hemoglobin concentration of erythrocytes", Biosensors and Bioelectronics 57 (2014) 59-64, Elsevier B.V.

Hun Kim et al., "Hemoglobin assay in anemic patients with a photothermal spectral-domain optical coherence reflectometric sensor", Clinica Chimica Acta 439 (2015) 71-76, Elsevier B.V.

* cited by examiner

APPARATUS AND METHOD FOR MEASURING CONCENTRATION OF HEMOGLOBIN USING PHOTOTHERMAL EFFECT

BACKGROUND OF THE INVENTION

Field of the Invention

The present invention relates to an apparatus and method for measuring concentration of hemoglobin, and more particularly, to an apparatus and method for measuring concentration of hemoglobin using a photothermal effect.

Background of the Related Art

Generally, hemoglobin is the iron-containing protein in the red blood cells which transports oxygen existing in the blood. A lack of hemoglobin causes anaemia. The causes of the anaemia are very various, and the measurement of hemoglobin concentration is used to classify the causes of the anaemia. For example, if the anaemia occurs due to a lack of iron, red blood cell indices are decreased, and if the anaemia occurs due to a lack of vitamin B12 or a lack of folic acid, the red blood cell indices are increased. Further, the anaemia occurs due to other causes, and since the red blood cell indices are differently provided in accordance with the causes of the anaemia, it is very important to measure a hemoglobin content in diagonosing the anaemia. Also, the hemoglobin content is a sensitive index indicating a lack of iron, and the index is used to diagnose diseases due to a lack of iron or to monitor efficiencies of iron therapy in veins.

Like this, as the hemoglobin content is used to diagnose various diseases, various technologies on the measurement of the hemoglobin concentration in the blood have been developed. Among them, a standard technology is provided by destroying the lipid bilayer of hemoglobin with potassium cyanide (KCN) and by conducting colorimetric analysis for the hemoglobin. However, poisonous toxic chemicals should be used whenever the hemoglobin concentration is measured. As other technologies, an electric-chemical method and immunoassay have been suggested, but unfortunately, the methods have a high degree of dependence on modelling, a low degree of accuracy, additional sensors using micro-electromechanical system (HEMS) or electrochemistry, and a long period of time required to measure the hemoglobin concentration.

SUMMARY OF THE INVENTION

Accordingly, the present invention has been made in view of the above-mentioned problems occurring in the prior art, and it is an object of the present invention to provide an apparatus and method for measuring concentration of hemoglobin using a photothermal effect that is simply configured to have a reference light source unit radiating a reference beam, a photothermal light source unit radiating a photothermal beam from which the photothermal effect is generated, and a cuvette unit accommodating a collected blood sample thereinto, thus measuring hemoglobin concentration with a high degree of accuracy, without having any addition of chemicals.

It is another object of the present invention to provide an apparatus and method for measuring concentration of hemoglobin using a photothermal effect that is capable of accurately measuring hemoglobin concentration by using phase changes of interference signals generated from the incidence of a reference beam radiated from a reference light source unit onto a cuvette unit as a photothermal beam radiated from a photothermal light source unit is incident onto the cuvette unit and absorbed by hemoglobin to generate the photothermal effect through the emission of heat.

To accomplish the above-mentioned objects, according to a first aspect of the present invention, there is provided an apparatus for measuring concentration of hemoglobin in blood using a photothermal effect, the apparatus including: a reference light source unit for radiating a reference beam; a photothermal light source unit for radiating a photothermal beam from which the photothermal effect is generated; a cuvette unit for accommodating a collected blood sample thereinto and having first and second reflection layers; and a concentration operation unit for calculating the concentration of hemoglobin by using the phase changes of interference signals generated from the incidence of the reference beam radiated from the reference light source unit onto the first and second reflection layers of the cuvette unit as the photothermal beam radiated from the photothermal light source unit is incident onto the cuvette unit and absorbed by hemoglobin to generate the photothermal effect through the emission of heat.

According to the present invention, preferably, the reference beam has a given wavelength in which no photothermal effect is generated from hemoglobin.

According to the present invention, preferably, the photothermal beam has a given wavelength in which the photothermal effect is generated from hemoglobin.

According to the present invention, preferably, the photothermal beam has the given wavelength in the range of 250 to 600 nm.

According to the present invention, preferably, the reference light source unit includes a reference beam generator adapted to radiate broadband light therefrom, and the reference beam generator includes any one selected in SLED (superluminescent light-emitting diode), LED (light-emitting diode), supercontinuum laser, wavelength-swept (tunable) laser, fiber laser, DFB (distributed feedback) laser, VCSEL (vertical cavity surface emitting) laser and DPSS (diode pumped solid state) laser.

According to the present invention, Preferably, the reference light source unit further comprises a light signal transmitter adapted to transmit the light signal radiated from the reference beam generator to the cuvette unit and to transmit the interference signals reflected and returned from the cuvette unit to the concentration operation unit.

According to the present invention, preferably, the light signal transmitter includes any one selected in a fiber optic coupler, fiber optic splitter, free space interferometer and beam splitter.

According to the present invention, preferably, the first reflection layer is formed of a transparent material to which light is transmitted, and the blood sample is located between the first reflection layer and the second reflection layer.

According to the present invention, preferably, the photothermal light source unit includes any one selected in a DPSS (diode pumped solid state) laser, LED (light-emitting diode), laser diode, dye laser, gas laser, argon laser and krypton laser.

According to the present invention, preferably, the apparatus further includes a modulation generating unit located in front of the photothermal light source unit to provide modulation to the photothermal beam radiated from the photothermal light source unit.

According to the present invention, preferably, the modulation generating unit includes any one selected in an embedded electronic modulator, optical shutter, optical chopper, AOM (acousto-optic modulator) and EOM (electro-optic modulator).

According to the present invention, preferably, the concentration operation unit reads the reflected interference signals through a spectrometer, reads absolute values of complex numbers obtained through inverse Fourier transform of the interference signals, finds the path-length having the greatest absolute value, and obtains the phase in the signal of the path-length.

According to the present invention, preferably, the concentration operation unit reads the reflected interference signals through a spectrometer, reads absolute values of complex numbers obtained through inverse Fourier transform of the interference signals, finds the path-length having the greatest absolute value, and obtains the phase in the signal of the path-length, while calculating the hemoglobin concentration with a peak value in a modulation frequency through Fourier transform of the phase change information, of the interference signals modulated by the modulation generating unit.

To accomplish the above-mentioned objects, according to a second aspect of the present invention, there is provided method for measuring concentration of hemoglobin using a hemoglobin concentration measuring apparatus, the apparatus including a reference light source unit for radiating a reference beam, a photothermal light source unit for radiating a photothermal beam from which the photothermal effect is generated, a cuvette unit for accommodating a collected blood sample thereinto and having first and second reflection layers, and a concentration operation unit for calculating the concentration of hemoglobin by using the phase changes of interference signals generated from the incidence of the reference beam radiated from the reference light source unit onto the first and second reflection layers of the cuvette unit as the photothermal beam radiated from the photothermal light source unit is incident onto the cuvette unit and absorbed by hemoglobin to generate the photothermal effect through the emission of heat, the method including the steps of: providing the blood sample to the cuvette unit; allowing the reference light source unit to radiate the reference beam; allowing the reference beam radiated from the reference light source unit to be incident onto the cuvette unit and reflected onto the first and second reflection layers of the cuvette unit and detecting the phases of the interference signals generated from the reflection of the reference beam; allowing the photothermal light source unit to radiate the photothermal beam; allowing the photothermal beam radiated from the photothermal light source unit to be incident onto the cuvette unit and to be absorbed by hemoglobin to generate the photothermal effect through the emission of heat; allowing the reference beam radiated from the reference light source unit to be incident onto the cuvette unit and reflected onto the first and second reflection layers of the cuvette unit and detecting the phases changes of the interference signals generated from the reflection of the reference beam; and operating the hemoglobin concentration in accordance with the relationship between the phase changes of the interference signals and the hemoglobin concentration.

BRIEF DESCRIPTION OF THE DRAWINGS

The above and other objects, features and advantages of the present invention will be apparent from the following detailed description of the preferred embodiments of the invention in conjunction with the accompanying drawings, in which:

FIGS. 4A to 4C are graphs showing phase changes generated from the photothermal effect in the apparatus for measuring concentration of hemoglobin according to the present invention, wherein FIG. 4A shows the phase change only when a reference beam is incident, FIG. 4B shows the phase change generated when a photothermal beam is incident, while the reference beam is being incident, and FIG. 4C shows the phase change generated when a photothermal beam is incident with the application of modulation, while the reference beam is being incident;

DETAILED DESCRIPTION OF THE PREFERRED EMBODIMENTS

Hereinafter, an explanation on an apparatus and method for measuring concentration of hemoglobin using a photothermal effect according to the present invention will be in detail given with reference to the attached drawing.

Figure 1:
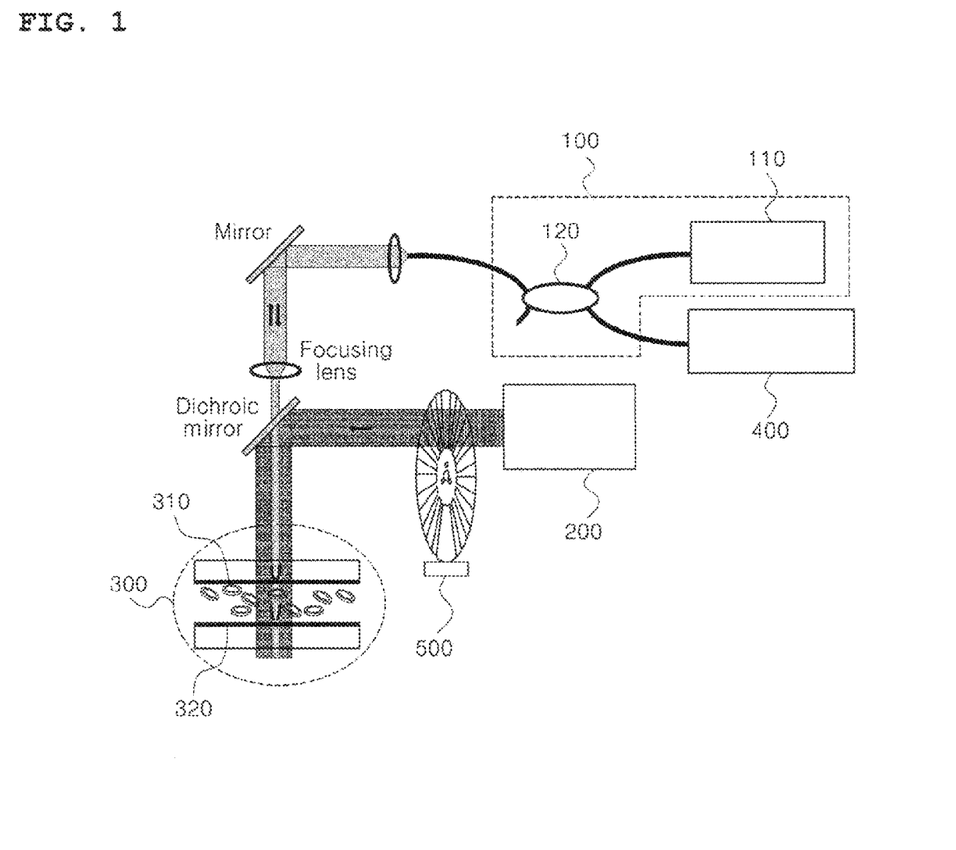
FIG. 1 is a block diagram showing a configuration of an apparatus for measuring concentration of hemoglobin using a photothermal effect according to the present invention.

FIG. 1 is a block diagram showing a configuration of an apparatus for measuring concentration of hemoglobin using a photothermal effect according to the present invention. So as to measure the concentration of hemoglobin in blood, light having two different wavelengths is incident onto a small quantity of blood sample obtained from blood to generate optical interference signals and a photothermal effect from the light having the two different wavelengths, and at this time, the present invention has the basic concept wherein the phase changes of the interference signals caused by the photothermal effects correspond to hemoglobin concentrations.

As shown in FIG. 1, the apparatus for measuring concentration of hemoglobin according to the present invention serves to measure the concentration of hemoglobin in blood using a photothermal effect and includes: a reference light source unit 100 for radiating a reference beam; a photothermal light source unit 200 for radiating a photothermal beam from which the photothermal effect is generated; a cuvette unit 300 for accommodating a collected blood sample thereinto; and a concentration operation unit 400 for calculating the concentration of hemoglobin by using the phase changes of interference signals generated from the incidence of the reference beam radiated from the reference light source unit 100 onto first and second reflection layers 310 and 320 of the cuvette unit 300 as the photothermal beam radiated from the photothermal light source unit 200 is incident onto the cuvette unit 300 and absorbed by hemoglobin to generate the photothermal effect through the emission of heat.

The reference light source unit 100 is configured to radiate the reference beam, and so as to adopt the principle of an optical interferometer, the reference light source unit 100 includes a reference beam generator 110 adapted to radiate broadband light therefrom, the reference beam generator 110 having any one selected in SLED (superluminescent light-emitting diode), LED (light-emitting diode), supercontinuum laser, wavelength-swept (tunable) laser, fiber laser, DFB (distributed feedback) laser, VCSEL (vertical cavity surface emitting) laser DPSS (diode pumped solid state) laser.

Figure 2:
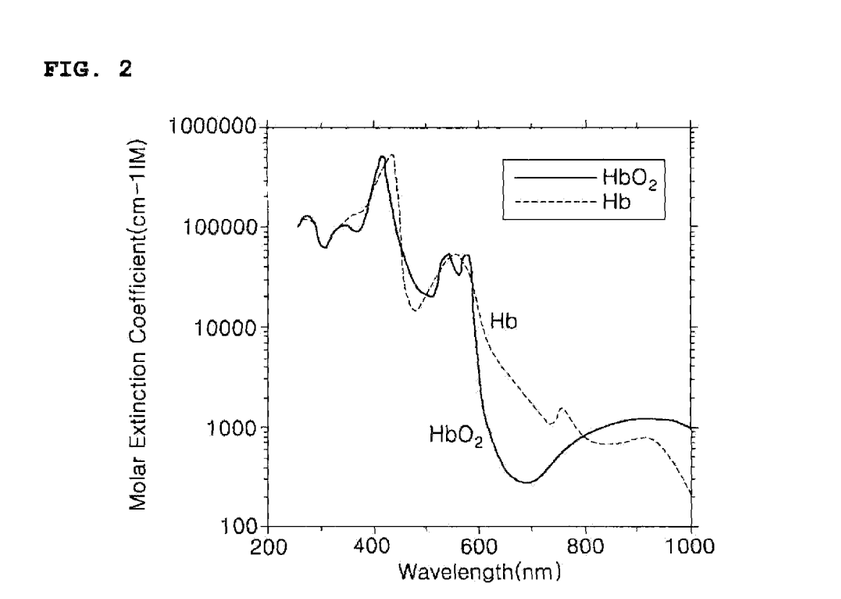
FIG. 2 is a graph showing absorption spectrum of hemoglobin according to the present invention.

At this time, the reference beam should be reflected onto the blood sample, not absorbed by the blood sample, thus checking phase change thereof. FIG. 2 is a graph showing absorption spectrum of hemoglobin according to the present invention, and as shown in FIG. 2, the absorption spectrum of hemoglobin becomes strong in the wavelength of 532 nm. When the absorption rate in the wavelength of 800 nm or more is compared with that in the wavelength of 532 nm, the hemoglobin of about 1% is absorbed in the wavelength of 800 nm or more, so that the beam having the wavelength in the range of 800 to 2000 nm which has a low absorption rate in absorption by the blood sample is used as the reference beam. That is, the beam having the range of wavelength not influenced by the photothermal effect is used as the reference beam.

Further, the reference light source unit 100 further includes a light signal transmitter 120 adapted to transmit the light signal radiated from the reference beam generator 110 to the cuvette unit 300 and to transmit the interference signals reflected and returned from the cuvette unit 300 to the concentration operation unit 400.

The light signal transmitter 120 includes any one selected in a fiber optic coupler, fiber optic splitter, free space interferometer and beam splitter.

The photothermal light source unit 200 serves to radiate the beam having the wavelength range having a high absorption rate to generate the photothermal effect. The wavelength range having the highest absorption rate is 532 nm, but it may be between 300 and 600 nm, without being limited thereto. If the wavelength range is shorter than 300 nm, the absorption of hemoglobin becomes stronger, but since it is limited in the depth capable of penetrating the blood, the wavelength range between 300 and 600 nm is most desirable.

The photothermal light source unit 200 includes any one selected in a DPSS (diode pumped solid state) laser, LED (light-emitting diode), laser diode, dye laser, gas laser, argon laser and krypton laser, and only if the photothermal light source unit 200 radiates the beam having the wavelength range as mentioned above, it may be not limited to the DPSS laser.

Further, a modulation generating unit 500 is located in front of the photothermal light source unit 200 to provide the modulation to the beam radiated from the photothermal light source unit 200, and the modulation generating unit 500 includes any one selected in an embedded electronic modulator, optical shutter, optical chopper, AOM (acousto-optic modulator) and EOM (electro-optic modulator). The formation of modulation enables the photothermal effect to be turned on/off at a given time interval, and through the application of the modulation, accordingly, the increment and decrement in the phase changes are repeatedly conducted. The values of the increment and decrement in the phase changes are stored in accordance with time, and if the stored values are operated, a signal-to-noise ratio is improved to obtain more accurate results.

The cuvette unit 300 is formed of a transparent material to which light is transmitted and includes the first reflection layer 310 and the second reflection layer 320. The blood sample is located between the first reflection layer 310 and the second reflection layer 320.

The concentration operation unit 400 reads the interference signal reflected in the above-mentioned configuration from a spectrometer, reads absolute values of complex numbers obtained through inverse Fourier transform of the interference signals, finds the path-length having the greatest absolute value, and obtains the phase in the signal of the path-length found from the interference signals. While the phases of the interference signals of the reference beam are being obtained, accordingly, the phases of the interference signals of the reference beam changed in accordance with the generation of the photothermal effect are obtained.

At this time, the peak values in modulation frequencies through the Fourier transform of the phase change information of the interference signals modulated by the modulation generating unit 500 are called 'PT SD-OCR (PhotoThermal Spectral-Domain Optical Coherence Reflectometry) signals'. The PT SD-OCR signals are compared with data obtained by existing reference, thus measuring the concentration of hemoglobin.

Figure 3:
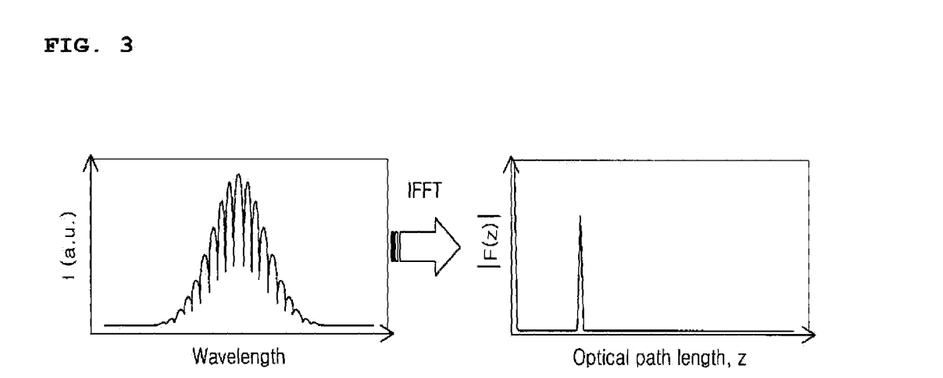
FIG. 3 is a graph showing an example of inverse Fourier transform of a concentration operation unit in the apparatus for measuring concentration of hemoglobin according to the present invention.

FIG. 3 is a graph showing an example of the inverse Fourier transform in the concentration operation unit of the apparatus for measuring concentration of hemoglobin according to the present invention. Referring to FIG. 3, the interference signals of the broadband beam reflected on the surface of the blood sample from the reference light source unit 100 are read by the spectrometer. The light reflected on the surface of the blood sample is mixed to generate interferences, and the interference signals generated by the interferences are read. If the inverse Fourier transform for the interference signals read by the spectrometer is conducted, the interference signals become complex-value data which is changed to data F(z) of optical path-length domain (new x-axis, z) in the wavelength domain (x-axis of the interference signals, k), and the phase information of the signal corresponding to the path-length having the greatest absolute value of the complex value data is obtained. That is, the signal corresponding to the path-length having the peak (maximum value) in the optical path-length domain is generated from the interferences between the beams reflected and returned from the first reflection layer 310 and the second reflection layer 320 in the cuvette unit 300 in which the blood sample is provided, thus continuously recording the phase information of the signal corresponding to the optical path-length from the beams reflected from the first reflection layer 310 and the second reflection layer 320.

While the phase information is being continuously obtained, at this time, the photothermal light source unit 200 applies the light having a wavelength in which the photothermal effect is generated well from erythrocyte to the blood sample. The applied photothermal beam is transmitted to the blood sample, while being modulated by the modulation generating unit 500, thus providing phase changes.

Figure 4A:
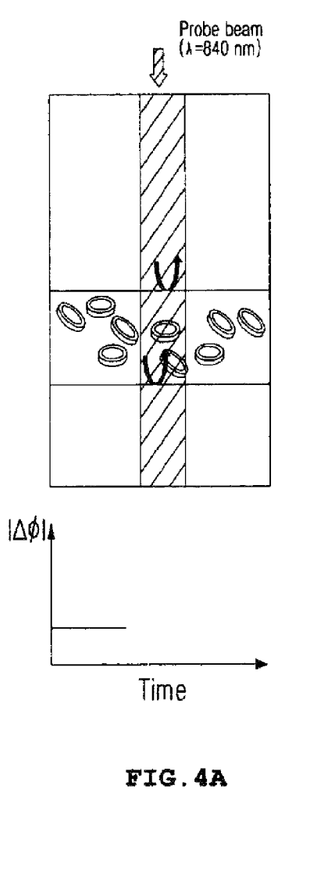
Figure 4B:
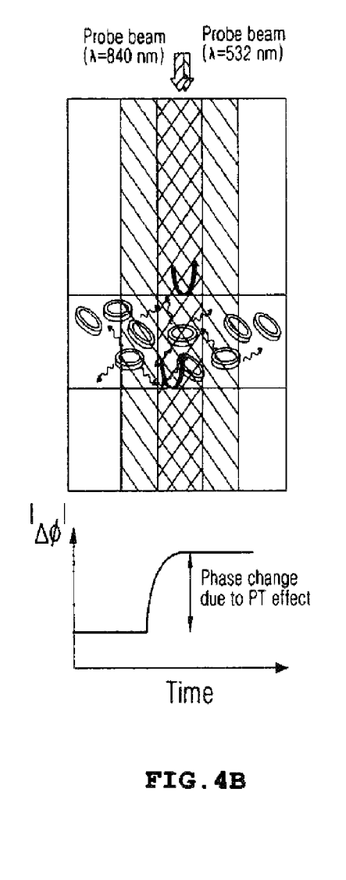
Figure 4C:
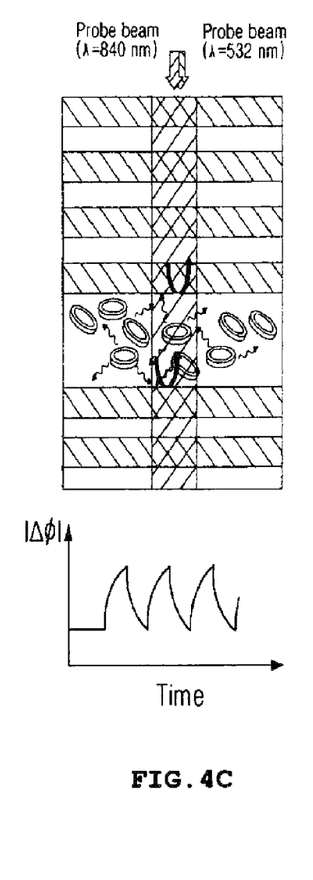

FIGS. 4A to 4C are graphs showing phase changes generated from the photothermal effect in the apparatus for measuring concentration of hemoglobin according to the present invention, wherein FIG. 4A shows the phase change only when a reference beam is incident, FIG. 4B shows the phase change generated when a photothermal beam is incident, while the reference beam is being incident, and FIG. 4C shows the phase change generated when a photothermal beam is incident with the application of modulation, while the reference beam is being incident.

Referring to FIGS. 4A to 4C, FIG. 4A shows the phase information wherein the photothermal beam is not applied, and in case where the photothermal effect is not generated, the interference of light is constant to cause no phase change in accordance with time. FIG. 4B shows the phase change generated when a photothermal beam is incident while the reference beam is being incident. The hemoglobin in the blood sample absorbs the photothermal beam, thus emitting heat (generating the photothermal effect). Since the blood sample is thermally expanded by the heat emitted, at this time, the refractive indexes of the blood sample become changed. As the refractive indexes become changed, the difference between the optical path-lengths of the light reflected on the first reflection layer 310 and the light reflected on the second reflection layer 320 of the cuvette unit 300 occurs, so that the phases of the interference signals read continuously become changed. As time is passed, however, saturation of the photothermal effect occurs, thus causing no more change in the phases of the interference signals. FIG. 4C shows the phase change generated when the photothermal beam is incident with the application of modulation, while the reference beam is being incident. Accordingly, the phase values are repeatedly increased and decreased at the time interval corresponding to the modulation frequency applied to the photothermal beam. At this time, the signal-to-noise ratio is improved with the values obtained through the modulation, thus obtaining more accurate results.

Figure 5A:
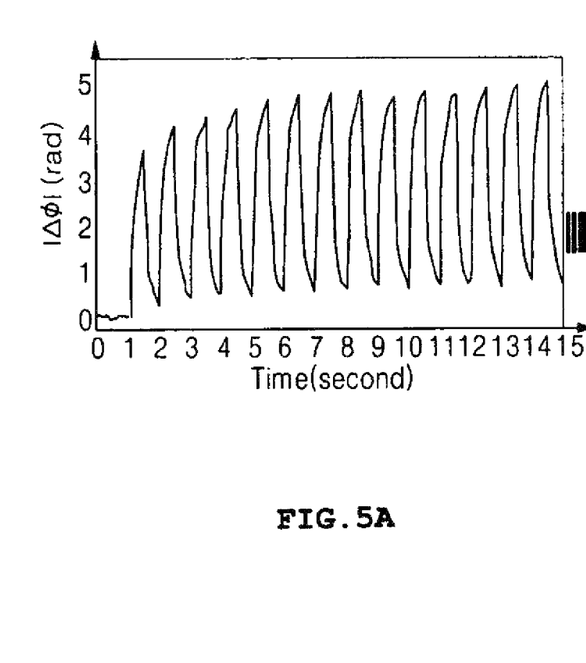
FIGS. 5A and 5B are graphs showing an example wherein PT SD-OCR signals are obtained by Fourier transform of phase change information in the concentration operation unit of the apparatus for measuring concentration of hemoglobin according to the present invention.
Figure 5B:
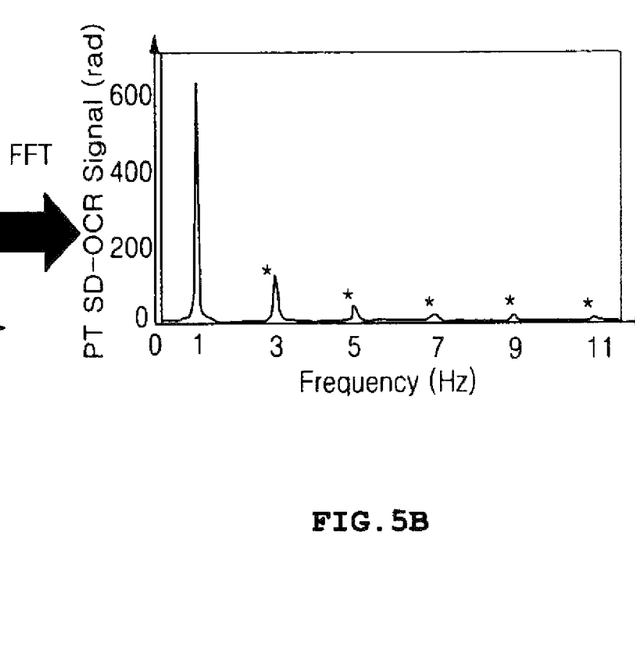

FIGS. 5A and 5B are graphs showing an example wherein PT SD-OCR signals are obtained by Fourier transform of phase change information in the concentration operation unit of the apparatus for measuring concentration of hemoglobin according to the present invention. FIG. 5A shows the phase information according to time. A section is taken by given time from the phase information, and Fourier transform for the phase information is conducted to obtain the result as shown in FIG. 5B. At this time, if a first peak value corresponding to the modulation frequency is taken in FIG. 5b, the first peak value becomes the PT SD-OCR signal in accordance with specific hemoglobin concentration and photothermal beam intensity. At this time, data corresponding to the frequencies to which a symbol * is attached can be ignored as harmonic frequencies.

Figure 6:
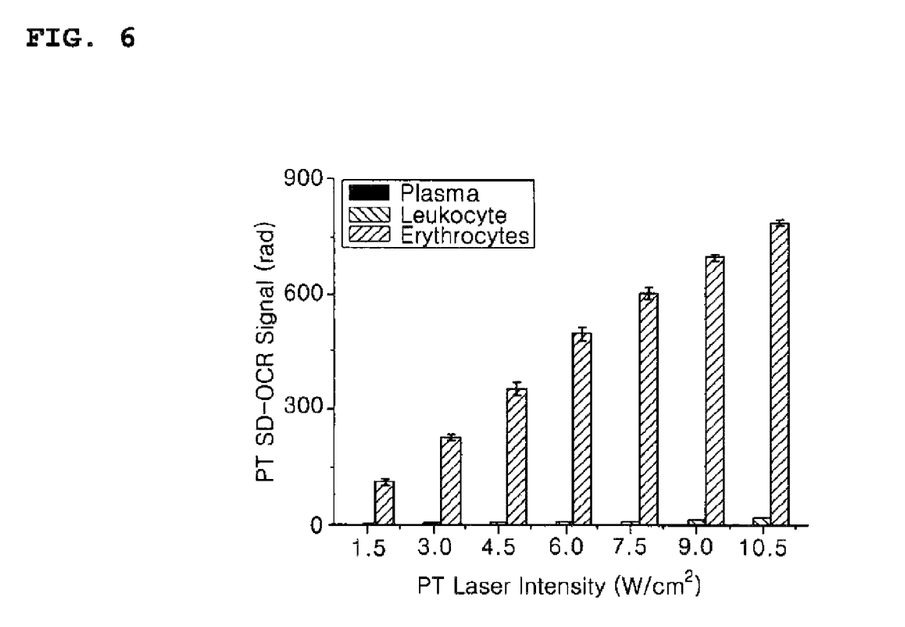
FIG. 6 is a graph showing the changes of PT SD-OCR signals in plasma, leukocyte and erythrocyte as components of blood in accordance with photothermal laser intensities.

FIG. 6 is a graph showing the changes of PT SD-OCR signals in plasma, leukocyte and erythrocyte as components of blood in accordance with photothermal laser intensities. Referring to FIG. 6, the PT SD-OCR signals are measured for the components of blood obtained by the centrifugal separation to measure the concentration of hemoglobin in the blood. The PT SD-OCR signals in the plasma and leukocyte are rarely found when compared to the erythrocyte blood sample (15.0 g/dL). At this time, it is hard to completely separate the leukocyte from the blood, and accordingly, the leukocyte blood sample in which the erythrocyte of about 0.3 g/dL is contained is provided. Therefore, it is found that there is no photothermal effect on the whole components of the blood except the erythrocyte.

Figure 7A:
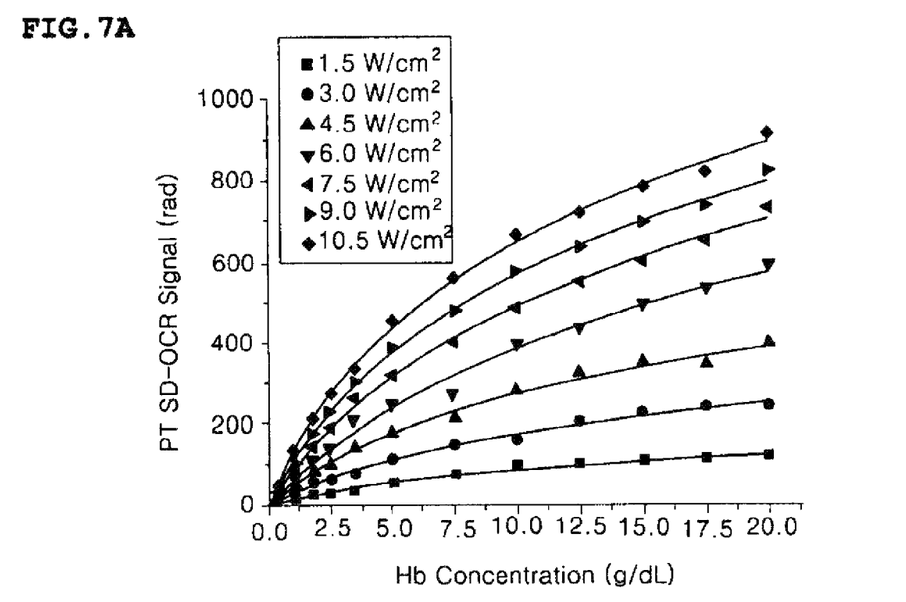
FIGS. 7A and 7B are graphs showing the changes of PT SD-OCR signals in accordance with the changes of hemoglobin concentration and photothermal laser intensity.
Figure 7B:
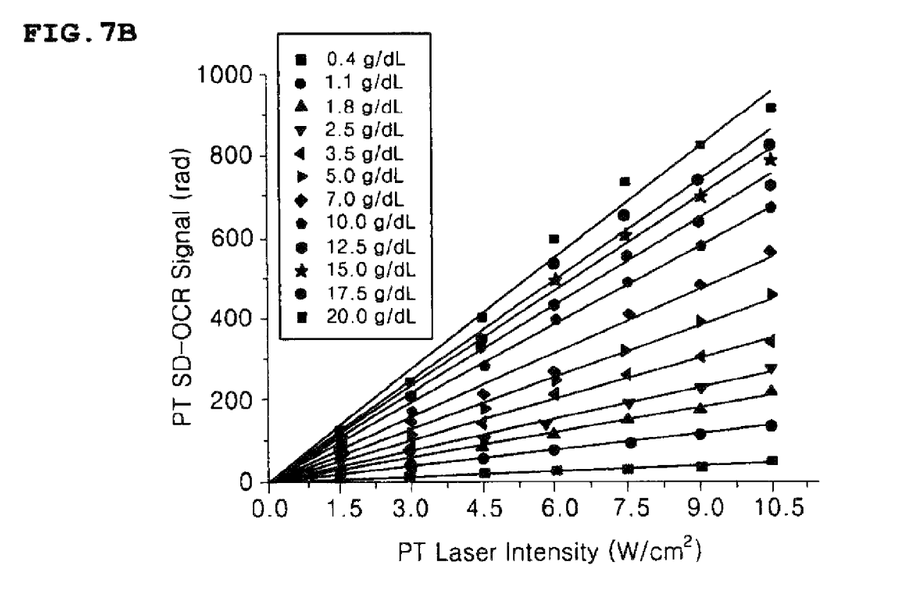
Figure 8:
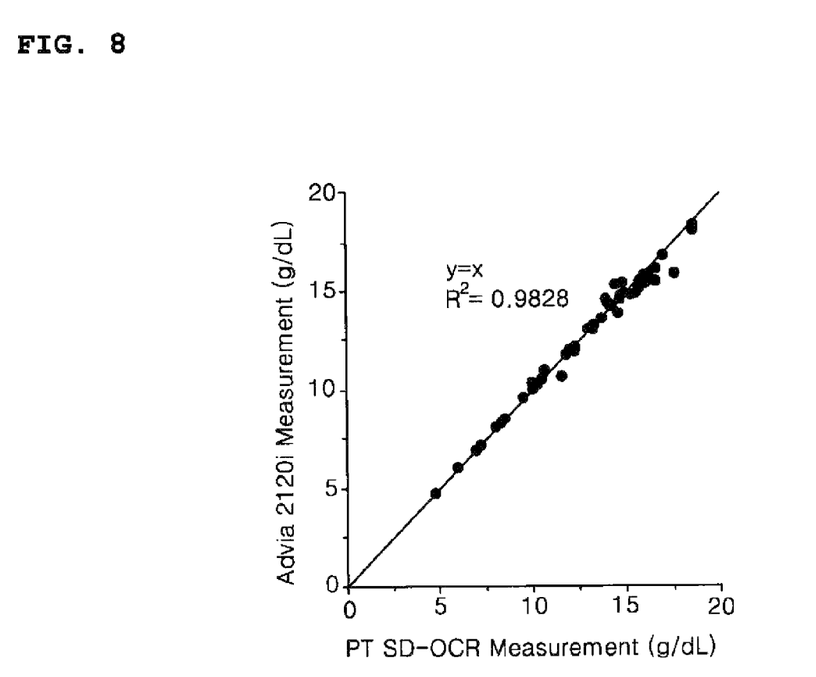
FIG. 8 is a graph showing the comparison between the measured results of the apparatus for measuring concentration of hemoglobin according to the present invention and the analyzed results of a standard method in hemoglobin concentration measurement.

FIGS. 7A and 7B are graphs showing the changes of PT SD-OCR signals in accordance with hemoglobin concentrations and photothermal laser intensities, and FIG. 8 is a graph showing the comparison between the measured results of the apparatus for measuring concentration of hemoglobin according to the present invention and the analyzed results of a standard method in hemoglobin concentration measurement. Referring to FIGS. 7A to 8, the PT SD-OCR signals are measured in accordance with hemoglobin concentrations and photothermal laser intensities. FIG. 7A shows the graph having an x-axis indicating hemoglobin concentrations, and FIG. 7B shows the graph having an x-axis indicating photothermal laser intensities. If curve fitting for the obtained data is conducted, the data in FIG. 7A has log functions, and the data in FIG. 7B has linear functions. The log functions in FIG. 7A are like the results of the previous study using the existing photothermal effect of gold nanorods.

The PT SD-OCR signals of the blood samples having given hemoglobin concentrations are measured to estimate the hemoglobin concentrations. After the PT SD-OCR signal values of 50 blood samples having given hemoglobin concentrations are measured, the curve fitting for the measured signal values is conducted as shown in FIG. 7A, thus estimating the hemoglobin concentrations. The estimated values of the hemoglobin concentrations are compared with the results of the hematology analyzer using the standard method (hemoglobin molecules are deformed by toxic material and a quantity of hemoglobin molecules deformed is measured) in the measurement of hemoglobin concentration, which is shown in FIG. 8.

As described above, the apparatus and method for measuring concentration of hemoglobin using the photothermal effect according to the present invention is simply configured to have the reference light source unit radiating the reference beam, the photothermal light source unit radiating the photothermal beam from which the photothermal effect is generated, and the cuvette unit accommodating the collected blood sample thereinto, thus measuring hemoglobin concentration with a high degree of accuracy, without having any addition of chemicals.

Further, the apparatus and method for measuring concentration of hemoglobin using the photothermal effect according to the present invention is capable of accurately measuring hemoglobin concentration by using phase changes of interference signals generated from the incidence of the reference beam radiated from the reference light source unit onto the cuvette unit as the photothermal beam radiated from the photothermal light source unit is incident onto the cuvette unit and absorbed by hemoglobin to generate the photothermal effect through the emission of heat.

While the present invention has been described with reference to the particular illustrative embodiments, it is not to be restricted by the embodiments but only by the appended claims. It is to be appreciated that those skilled in the art can change or modify the embodiments without departing from the scope and spirit of the present invention.

What is claimed is:

1. An apparatus for measuring concentration of hemoglobin in blood using a photothermal effect, the apparatus comprising:
   a reference light source radiating a reference beam;
   a photothermal light source radiating a photothermal beam from which the photothermal effect is generated;
   a cuvette accommodating a collected blood sample thereinto and having first and second reflection layers; and
   a concentration operator loaded on and executed by a hardware processor and calculating the concentration of hemoglobin by using the phase changes of interference signals generated from the incidence of the reference beam radiated from the reference light source onto the first and second reflection layers of the cuvette unit as the photothermal beam radiated from the photothermal light source is incident onto the cuvette and absorbed by hemoglobin to generate the photothermal effect through the emission of heat, wherein the concentration operator reads the reflected interference signals through a spectrometer, reads absolute values of complex numbers obtained through inverse Fourier transform of the interference signals, finds the path-length having the greatest absolute value, and obtains the phase in the signal of the path-length.

2. The apparatus according to claim 1, wherein the reference beam has a given wavelength in which no photothermal effect is generated from hemoglobin.

3. The apparatus according to claim 1, wherein the photothermal beam has a given wavelength in which the photothermal effect is generated from hemoglobin.

4. The apparatus according to claim 3, wherein the photothermal beam has the given wavelength in the range of 250 to 600 nm.

5. The apparatus according to claim 1, wherein the reference light source comprises a reference beam generator adapted to radiate broadband light therefrom, and the reference beam generator includes any one selected in SLED (superluminescent light-emitting diode), LED (light-emitting diode), supercontinuum laser, wavelength-swept (tunable) laser, fiber laser, DFB (distributed feedback) laser, VCSEL (vertical cavity surface emitting) laser and DPSS (diode pumped solid state) laser.

6. The apparatus according to claim 5, wherein the reference light source further comprises a light signal transmitter adapted to transmit the light signal radiated from the reference beam generator to the cuvette and to transmit the interference signals reflected and returned from the cuvette to the concentration operator.

7. The apparatus according to claim 6, wherein the light signal transmitter comprises any one selected in a fiber optic coupler, fiber optic splitter, free space interferometer and beam splitter.

8. The apparatus according to claim 1, wherein the first reflection layer is formed of a transparent material to which light is transmitted, and the blood sample is located between the first reflection layer and the second reflection layer.

9. The apparatus according to claim 1, wherein the photothermal light source comprises any one selected in a DPSS (diode pumped solid state) laser, LED (light-emitting diode), laser diode, dye laser, gas laser, argon laser and krypton laser.

10. The apparatus according to claim 9, further comprising a modulation generator located in front of the photothermal light source to provide modulation to the photothermal beam radiated from the photothermal light source.

11. The apparatus according to claim 10, wherein the modulation generator comprises any one selected in an embedded electronic modulator, optical shutter, optical chopper, AOM (acousto-optic modulator) and EOM (electro-optic modulator).

12. The apparatus according to claim 10, wherein the concentration operator reads the reflected interference signals through a spectrometer, reads absolute values of complex numbers obtained through inverse Fourier transform of the interference signals, finds the path-length having the greatest absolute value, and obtains the phase in the signal of the path-length, while calculating the hemoglobin concentration with a peak value in a modulation frequency through Fourier transform of the phase change information of the interference signals modulated by the modulation generator.

13. The apparatus according to claim 11, wherein the concentration operator reads the reflected interference signals through a spectrometer, reads absolute values of complex numbers obtained through inverse Fourier transform of the interference signals, finds the path-length having the greatest absolute value, and obtains the phase in the signal of the path-length, while calculating the hemoglobin concentration with a peak value in a modulation frequency through Fourier transform of the phase change information of the interference signals modulated by the modulation generator.

14. A method for measuring concentration of hemoglobin using a hemoglobin concentration measuring apparatus, the apparatus comprising a reference light source radiating a reference beam, a photothermal light source radiating a photothermal beam from which the photothermal effect is generated, a cuvette accommodating a collected blood sample thereinto and having first and second reflection layers, and a concentration operator for calculating the concentration of hemoglobin by using the phase changes of interference signals generated from the incidence of the reference beam radiated from the reference light source onto the first and second reflection layers of the cuvette as the photothermal beam radiated from the photothermal light source is incident onto the cuvette and absorbed by hemoglobin to generate the photothermal effect through the emission of heat, the method comprising the steps of:

providing the blood sample to the cuvette;

allowing the reference light source to radiate the reference beam;

allowing the reference beam radiated from the reference light source unit to be incident onto the cuvette and reflected onto the first and second reflection layers of the cuvette and detecting the phases of the interference signals generated from the reflection of the reference beam;

allowing the photothermal light source to radiate the photothermal beam; allowing the photothermal beam radiated from the photothermal light source to be incident onto the cuvette and to be absorbed by hemoglobin to generate the photothermal effect through the emission of heat;

allowing the reference beam radiated from the reference light source to be incident onto the cuvette and reflected onto the first and second reflection layers of the cuvette and detecting the phases changes of the interference signals generated from the reflection of the reference beam; and operating the hemoglobin concentration in accordance with the relationship between the phase changes of the interference signals and the hemoglobin concentration, wherein the concentration operator reads the reflected interference signals through a spectrometer, reads absolute values of complex numbers obtained through inverse Fourier transform of the interference signals, finds the path-length having the greatest absolute value, and obtains the phase in the signal of the path-length.

* * * * *